United States Patent [19]
Cottone, Sr. et al.

[11] Patent Number: 5,385,558
[45] Date of Patent: Jan. 31, 1995

[54] ANGIOGRAPHIC CONTROL SYRINGE

[75] Inventors: Joseph R. Cottone, Sr., Marietta; Anthony J. Cottone, Ball Ground, both of Ga.

[73] Assignee: Maxxim Medical, Inc., Sugar Land, Tex.

[21] Appl. No.: 116,345

[22] Filed: Sep. 3, 1993

[51] Int. Cl.$^6$ .................. A61M 5/00; A61M 5/315
[52] U.S. Cl. .................................. 604/208; 604/225
[58] Field of Search .............. 222/309; 604/122, 187, 604/207–210, 218, 220, 225

[56] References Cited

U.S. PATENT DOCUMENTS

| | | | |
|---|---|---|---|
| 1,569,457 | 1/1926 | Carstens | 604/210 |
| 2,856,925 | 10/1958 | Helmer et al. | 604/210 |
| 3,752,145 | 8/1973 | Runnells et al. | 604/122 |
| 4,444,335 | 4/1984 | Wood et al. | 604/208 |
| 4,642,102 | 2/1987 | Ohmori | 604/210 |
| 4,654,035 | 3/1987 | Ando | 604/210 |
| 4,874,385 | 10/1989 | Moran et al. | 604/210 |
| 5,009,645 | 4/1991 | Silver et al. | 604/210 |

FOREIGN PATENT DOCUMENTS

| | | | |
|---|---|---|---|
| 0788225 | 10/1935 | France | 604/122 |
| PCT/US89/-00577 | 10/1989 | WIPO . | |

*Primary Examiner*—C. Fred Rosenbaum
*Assistant Examiner*—Frank Wilkens, III
*Attorney, Agent, or Firm*—Veal & Associates

[57] ABSTRACT

An improved angiographic control syringe for use in high-pressure medical procedures. An oblong locking ring disposed on a plunger stem. The oblong locking ring has two circular end segments at the far opposing ends of the ring, and comprises two flat segments at the narrow diameter opposing sides of the ring. A plurality of grooves are vertically spaced on the upper part of the plunger stem. Notches extend inwardly from the flat segments of the locking ring. The exertion of a pinching force on the circular end segments of the locking ring causes convex radial expansion of the flat segments, thereby permitting detachable engagement of the notches with any groove. The plunger head has a highly angular frustoconical head. The syringe barrel has a less angular frustoconical seat that receives the plunger head when the plunger head is fully depressed within the syringe barrel. Due to the difference between the angle of the plunger head and the angle of the seat, a circular air bubble retention cell is formed between the outer wall of the plunger head and the outer wall of the syringe barrel seat when the plunger is fully depressed.

8 Claims, 5 Drawing Sheets

ANGIOGRAPHIC CONTROL SYRINGE

TECHNICAL FIELD

The present invention relates to an improved control syringe for use in medical procedures and, more particularly, relates to a high-pressure, hand-held control syringe for injecting fluid into or retracting fluid from a patient during angiographic procedures.

BACKGROUND OF THE INVENTION

In many medical procedures, it is necessary to inject fluid into or withdraw fluid from a patient at relatively high-pressure. In addition, the amount of pressure needed to inject or withdraw fluid typically varies from procedure to procedure and from patient to patient. Therefore, the user must carefully monitor and control the syringe to ensure that the proper volume of fluid is dispensed or withdrawn at the appropriate rate. In such procedures, it is desirable to use hand-held syringes so that a trained medical staffperson can moderate and precisely control the amount of fluid injected into or withdrawn from the patient.

The need for syringes capable of injecting or withdrawing fluid at high pressure, wherein the volume of fluid injected or withdrawn can be carefully controlled, led to the development of hand-held "control" syringes. These control syringes are constructed much like traditional syringes, with a plunger slidably mating with the interior of a syringe barrel. Both the plunger and the syringe barrel in the control syringe are larger and made of stronger material than conventional syringes. These modifications allow the control syringes to withstand the higher pressures incurred in certain procedures.

Today, control syringes are used in a variety of medical procedures, especially angiographic procedures. For example, in one common use, a control syringe and a catheterization system are connected using a Luer connector. The control syringe is loaded with a dye that is injected into the coronary arteries of a patient. The dye usually must be injected under high pressure. An X-ray machine photographs the flow of dye through the cardiac system, thereby identifying any occlusions that are blocking blood flow in the coronary system. To accurately administer and calculate the flow of dye through the coronary system, both the pressure at which the dye is injected and the volume of dye injected must be controlled. Control syringes permit such high-pressure control of an injectate.

Control syringes are also used in other angiographic procedures, such as renal or carotid and angiographic procedures. The common use of control syringes in these procedures is the provision of a high-pressure, hand-held syringe capable of injecting or withdrawing specific volumes of fluid.

It is often the case in use of a control syringe that the user must exert maximum force on the plunger and syringe barrel to create the pressure needed to inject or withdraw fluid. Considering the amount of pressure that must be placed on the plunger and syringe barrel, it is not surprising that a common problem experienced when using control syringes is that users are unable to accurately control the volume of fluid expelled from or drawn into the syringe.

For example, presume the user must inject 2 cc of dye every 30 seconds for two minutes. The control syringe would be loaded with 8 cc of dye (2 cc×4 injections). The user may need to exert great force on the plunger to inject the fluid, while simultaneously controlling the plunger to inject only 2 cc at a time. In the past, users frequently applied pressure for too long and injected too much fluid. For example, the user might accidentally inject 4 cc of fluid instead of 2 cc, because the high pressure needed to move the plunger in the syringe barrel hindered the control of the plunger.

In order to control and limit the motion of the plunger within the syringe barrel, locking devices have been developed for angiographic control syringes. Typical locking devices are positioned on the plunger stem, and are movable along the vertical axis of the plunger stem. When the locking ring abuts the top of the syringe barrel, the plunger may be depressed no further within the syringe barrel. The locking device thus limits the amount of fluid that can be expelled from the syringe.

One such locking device is set forth in International Patent Application No. PCT/US89/0057, assigned to Merit Medical Systems Inc. ("Merit"). In Merit, a nut is slidably positioned on a plunger stem. A protruding member extends inwardly from the nut and engages a vertical slot on the plunger stem. The nut slides freely along the stem when the protruding member engages the vertical slot. A plurality of notches extend perpendicularly from the vertical slot. The protruding member on the nut may be aligned with a notch and, by rotating the nut, the protruding member engages the notch. When the protruding member engages one of the notches, the nut may not be vertically moved on the plunger stem. The nut limits how deep the plunger may be inserted into the syringe barrel, thereby limiting the amount of fluid that can be injected from the syringe control.

However, the above locking mechanism has deficiencies. In the Merit device, the nut has some rotational "play" when the protruding member is positioned in the vertical slot. The user may mistake this rotational play for the successful engagement of the protruding member with a notch. The nut does not preclude plunger movement if the nut is not locked into place. The danger of not properly inserting the protruding member within a notch is significant. For example, presume that the syringe barrel contains 10 cc of dye, but only 2 cc are to be injected at a time. The nut would be placed over a notch so that only 2 cc would be dispensed. However, if the protruding member does not fully engage the 2 cc notch, the protruding member will be aligned with the vertical slot. The user, expecting the nut to preclude the injection of more than 2 cc of fluid, will exert full pressure on the plunger stem. Instead of engaging the top of the syringe barrel to preclude downward motion of the plunger, the nut will slide in the vertical slot, resulting in injection of the full contents of the syringe. Further, if the protruding member only partially engages the notch, the nut may be dislocated from the notch by low force. This again may result in failure of the nut to preclude motion of the plunger in the syringe barrel.

A further problem with the Merit device is that the rotational movement required to lock and unlock the nut is a complex motion. The user of the control syringe is often using one hand to control the syringe barrel and the other hand to control the plunger. Also, each hand is usually pushing or holding part of the control syringe under great force. The need to apply pressure using both hands hinders rotational movement of either hand to control the nut.

Specifically, a user might hold the syringe barrel in their left hand. The user could then push or withdraw the plunger using their right hand. Both hands direct force onto the respective cylindrical objects (syringe and syringe barrel) under control. At least two fingers, typically the thumb and forefinger, must be relieved from holding the syringe or syringe barrel under force to control the locking nut. Tightly holding an object while trying to turn another object is awkward and difficult.

A different problem frequently encountered when using present control syringes is the presence of air bubbles within the injectate. The injection of an air bubble into a patient is undesirable and to be avoided. This problem led to the development of transparent angiographic syringes, which allow the user to view and screen the injectate for air bubbles. However, the users of control syringes sometimes do not see air bubbles in the injectate, especially small air bubbles. In present control syringes, the plunger head forces air bubbles downward toward the bottom of the syringe barrel. The frustoconical plunger head fully engages a seat at the bottom of the syringe barrel. Because the plunger head fully engages the seat of the syringe barrel, the entire contents of the control syringe are expelled. Therefore, any air bubbles in the syringe barrel are injected into the patient.

Accordingly, a need yet exists for an improved angiographic control syringe. Such a control syringe would have a locking mechanism that was easily adjustable and that locked securely and accurately into position. Further, such an improved control syringe would have means for capturing air bubbles in the injectate to limit the injection of the air bubbles into patients.

SUMMARY OF THE INVENTION

The present invention solves the above-identified problems in the art by providing an improved angiographic control syringe. The improved angiographic syringe has an improved locking ring for controlling the amount of fluid injected from or drawn into the syringe. Further, the improved angiographic syringe has an air bubble retention cell to decrease the likelihood of injecting air bubbles from the syringe into a patient.

Briefly described, the locking ring is an oblong ring disposed on the plunger stem. The oblong locking ring has two circular end-segments at the far opposing ends of the ring. Across the narrower diameter opposing sides of the oblong locking ring, between the circular end segments, the oblong locking ring comprises two flat segments.

Protrusions extend inwardly from the flat segments of the locking ring to engage any one of a plurality of grooves that are vertically spaced on the upper part of the plunger stem. The exertion of a pinching force on the circular end segments of the locking ring causes convex radial movement of the flat segments, thereby disengaging the protrusions from groove with which they are engaged. When the flat segments are moved outward by the pinching force, the locking ring is slidable along the stem and can be positioned over any groove. Release of the pinching force causes inward radial retraction of the flat segments of the locking ring, causing the protrusions to move inwardly and engage a groove.

The locking ring is thus positionable over any groove so that the protrusions engage the groove. With the notches on the locking ring engaged in a groove on the plunger stem, the plunger can be freely moved within the syringe barrel until the locking ring abuts the top of the syringe barrel. The locking ring abutting the syringe barrel precludes further depression of the plunger within the syringe barrel, thereby limiting the amount of fluid expelled from the syringe.

The pressure of the syringe barrel on the locking ring does not cause the locking ring of the present invention to slide. The pressure applied by the syringe barrel is perpendicular to the locking ring, and forces perpendicular to the locking ring only press the notches against the side walls of the grooves. To disengage the protrusions from a groove, without breaking the notches or the locking ring, a pinching force on the circular segments of the locking ring must be applied. Thus, the locking ring precludes downward movement of the plunger within the syringe barrel.

According to another aspect of the present invention, an air bubble retention cell is formed in the present invention to capture air bubbles. The plunger head has a highly angular frustoconical head. The syringe barrel has a less angular frustoconical seat that receives the plunger head when the plunger head is fully depressed within the syringe barrel. Due to the difference between the angle of the plunger head and the angle of the seat, a circular cell is formed between the outer wall of the plunger head and the outer wall of the syringe barrel seat when the plunger is fully depressed. When the plunger head is depressed, air bubbles will rise along the frustoconical surface of the plunger head, away from the opening in the syringe barrel seat, and be captured in the air bubble retention cell.

Accordingly, it is an object of the present invention to provide an improved angiographic control syringe.

It is a further object of this invention to provide a locking ring for control syringes that is easy to lock into position and can withstand high pressure.

It is a further object of this invention to provide a locking ring that responds to failure to lock the ring into position by automatically locking the ring into position when met with force from depression of the plunger in the syringe barrel.

It is a further object of this invention to provide a control syringe that reduces the possibility of injecting an air bubble into a patient.

Other objects, features and advantages of the present invention will become apparent upon review of the following detailed description of embodiments of the invention when taken in conjunction with the drawings and appended claims.

DETAILED DESCRIPTION OF THE DISCLOSED EMBODIMENT

Figure 6:
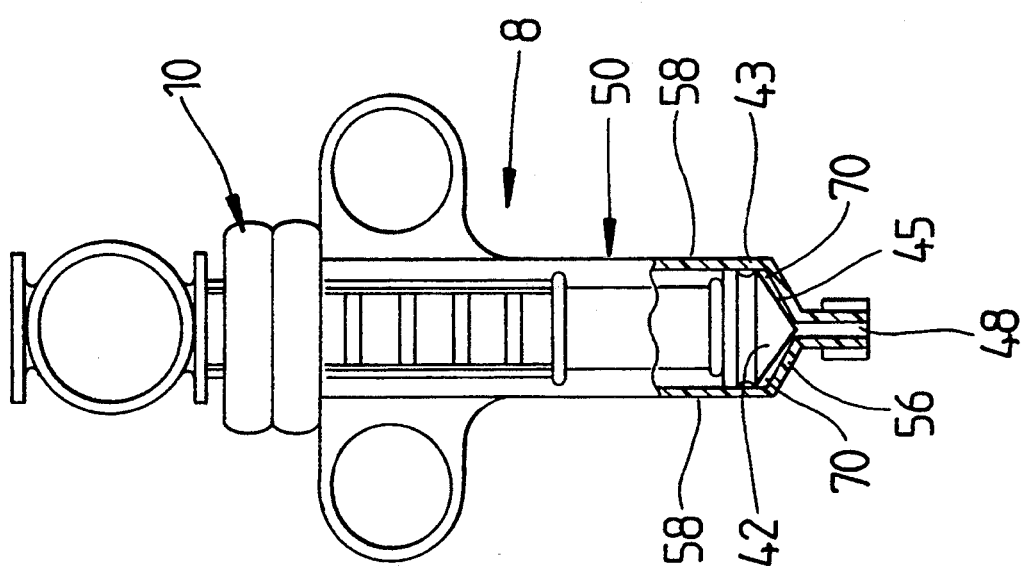
FIG. 6 is a side view of FIG. 1 showing the plunger head the syringe barrel engaging seat, and wherein no luer connector is attached to the syringe barrel.

Refer now to the Figures in which like referenced numerals correspond to like parts throughout the several views. FIG. I is a front perspective of an improved angiographic control syringe 8 constructed in accordance with the preferred embodiment of the present invention. The preferred angiographic control syringe 8 comprises a plunger 34, a locking ring 10 mounted on the plunger, a syringe barrel 50 matingly engaging the plunger, and, as shown in FIG. 6, an air bubble retention cell 70 formed between the plunger tip 42 and syringe barrel seat 56 when the plunger 34 and syringe barrel 50 are fully engaged.

Figure 1:
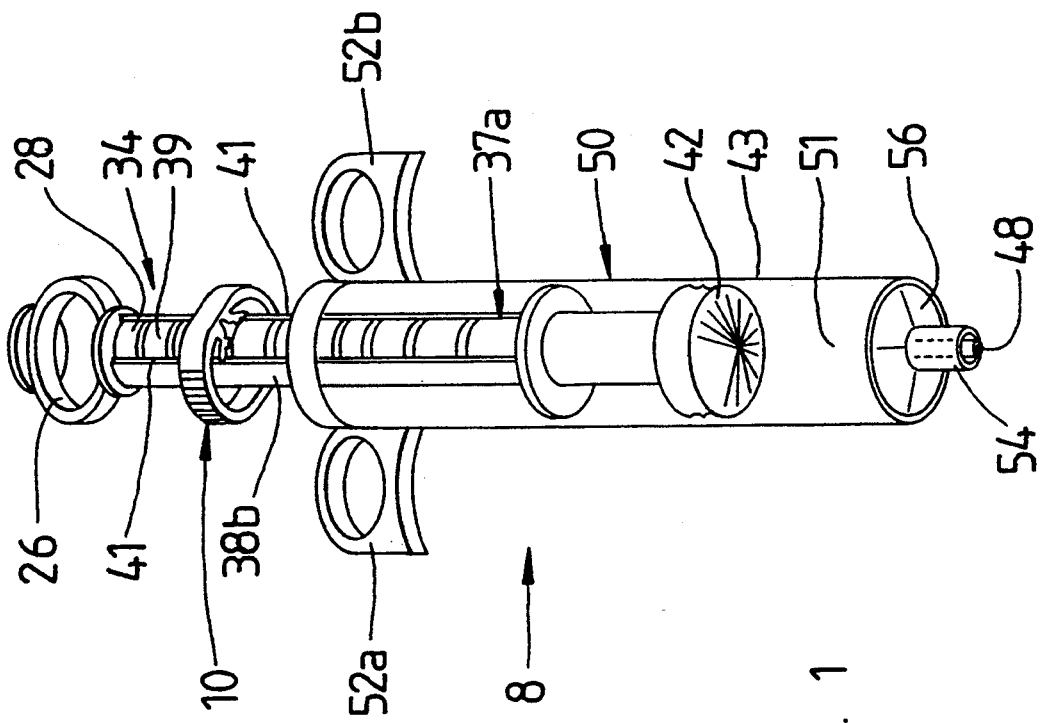
FIG. 1 is a front perspective view of an improved angiographic control syringe constructed in accordance with the preferred embodiment of the present invention.

Referring to FIG. 1, the syringe barrel 50 is preferably formed of a high strength, low cost, transparent material, preferably a polycarbonate plastic, such as LEXAN HP-111, manufactured by General Electric Company. As is familiar to those skilled in the art, a transparent syringe barrel is preferable because it allows the user to visually inspect the contents of the syringe barrel 50 for air bubbles and other impurities that are harmful if injected into the patient.

At the lower end of the syringe barrel 50 is a conventional female luer connector 54. A conventional male luer connection and catheter (not shown) is affixed to luer connector 54 during use of the preferred embodiment. Fluid passes from the syringe barrel bore 51 through opening 48 and out of luer connector 54, or vice versa if fluid is withdrawn from the patient. The use of a luer connection between the syringe 8 and the catheterization system allows axial rotation of syringe 8 relative to the system to which the control syringe 8 is affixed. The user of syringe 8 can thereby rotate the syringe so that it is in the most convenient position for use.

Continuing to view FIG. 1, two grasping rings 52a and 52b are on opposing sides of the syringe barrel 50. The grasping rings 52a and 52b are preferably injection molded with and made of the same material as the syringe barrel 50. The grasping rings 52a and 52b are suitable for receipt of the forefinger and index finger of the user, and rings 52a and 52b allow a user to firmly hold and control the syringe barrel 50.

The plunger 34 includes a stem 28 with a plunger tip 42 affixed on the lower end of the stem 28 and a thumb ring 26 integrally formed on the upper end of the stem 28. In the preferred embodiment, the plunger tip 42 is made of natural rubber. As can best be seen in FIG. 4A, an expansion fit between the elastic plunger tip 42 and plunger head 61 secures the plunger tip 42 in position on stem 28. Referring back to FIG. 1, the plunger tip 42 sealingly engages the syringe barrel 50. Fluid within syringe barrel bore 51 cannot flow past plunger side wall 43. The plunger tip 42 may be vertically displaced within the syringe barrel 50 by the application of pressure on plunger 34 using thumb ring 26. As is familiar to those skilled in the art, fluid is drawn into or expelled from the bore 51 of syringe barrel 50 as plunger tip 42 is vertically displaced.

Figure 3B:
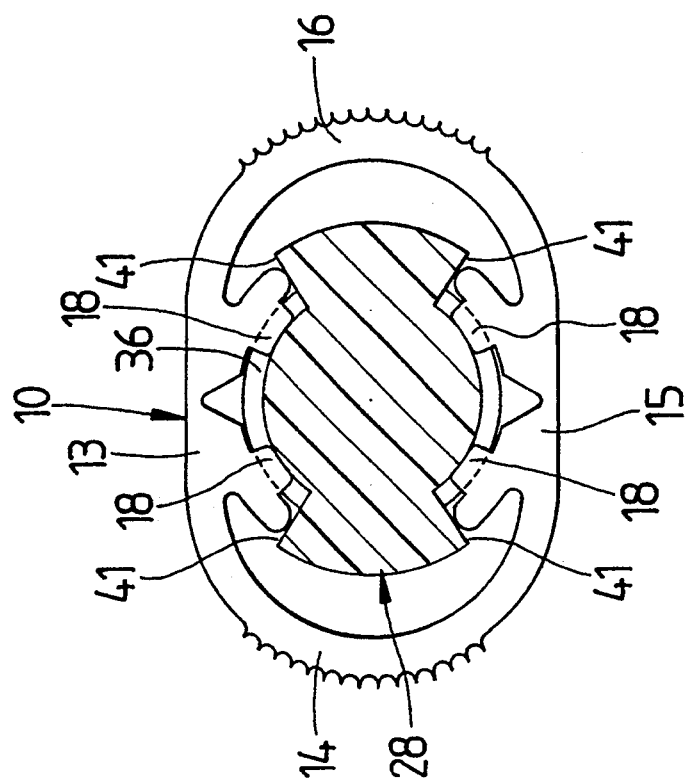
FIG. 3B is a bottom view of FIG. 3A, showing the locking ring mounted on the stem.
Figure 3A:
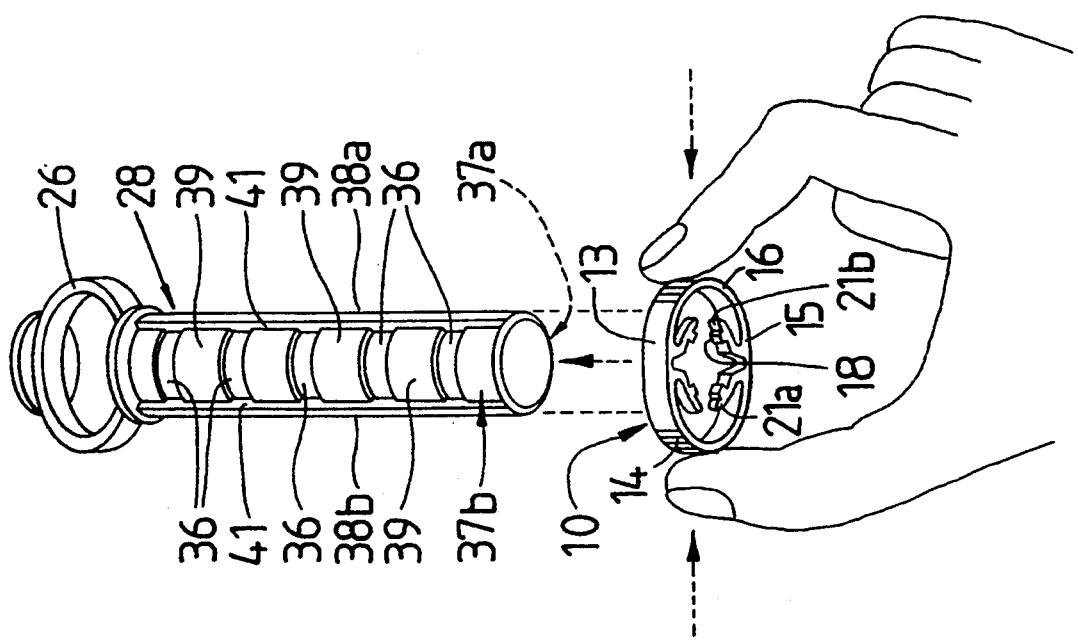
FIG. 3A is a perspective view of the locking ring about to be mounted onto the plunger stem, wherein the plunger stem does not have a plunger head.

Stem 28 of the plunger 34 is preferably formed of ABS plastic, made by Dow Chemical Corp. ABS plastic is used because it is low cost, high strength, light weight and easily injection molded. The thumb ring 26 and plunger head 61 are preferably made of the same material as, and molded as a unit with, stem 28. Referring now to FIG. 3A, annular grooves 36 are injection molded into the upper portion of stem 28. In the preferred embodiment, the annular grooves 36 are aligned in two columns 37a and 37b located on opposing faces of stem 28. The two columns of grooves 37a and 37b, and are divided by two columnular, arcuate smooth sections 38a and 38b. Each column of grooves 37a and 37b is about 110° in radius, and each columnular smooth section 38a and 38b is about 75° in radius. Those skilled in the art will recognize that the radial sizes of the columns of grooves 37a and 37b and the columnular smooth sections 38a and 38b can be varied.

Figure 2:
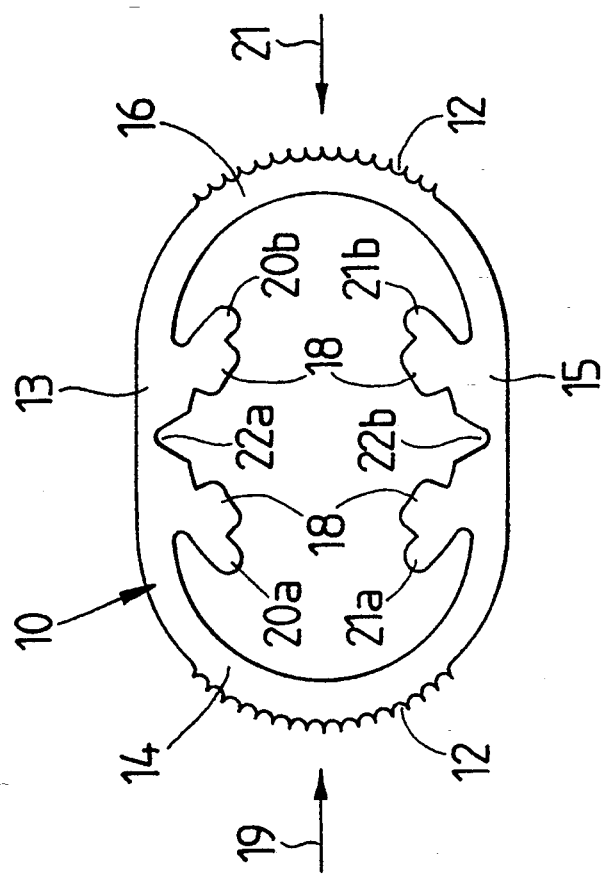
FIG. 2 is a top view of the locking ring of the preferred embodiment.
Figure 4:
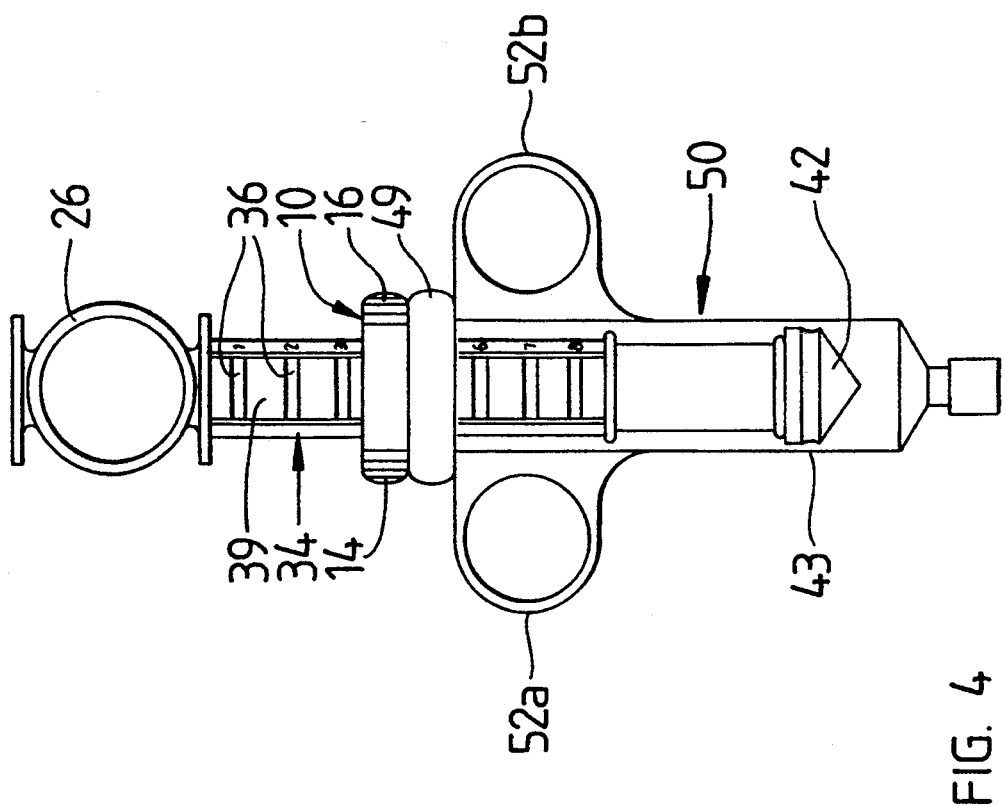
FIG. 4 is frontal view of the present invention, showing the top of the syringe barrel abutting the locking ring.
Figure 4A:
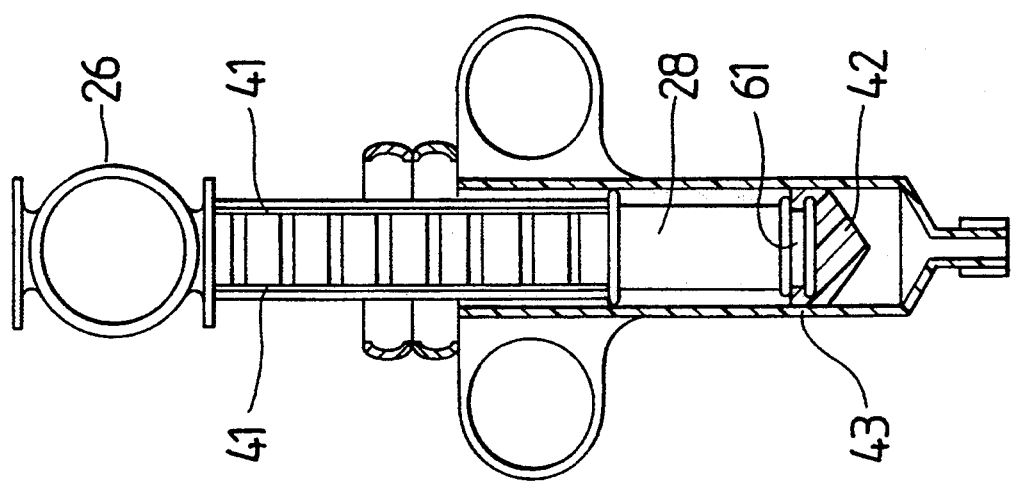
FIG. 4A is a frontal view of a cross-section of the present invention.

At the intersection of each column of grooves 37a and 37b, and each columnular, arcuate smooth section 38a and 38b, a vertical lip 41 is formed (FIGS. 3A and 4A). The slightly greater diameter of stem 28 across columnular arcuate smooth sections 38a and 38b compared to the smaller diameter across the columns of grooves 37a and 37b produces vertical lips 41. The purpose of vertical lips 41 is fully described below. A locking ring 10 is positionable on stem 28. FIG. 2 is a top view of the locking ring 10 of the preferred embodiment. The locking ring 10 is preferably made of propylene, a strong resilient material known to those skilled in the art.

The locking ring 10 is oblong in shape, with gripping ridges 12 on the circular segments 14 and 16. The ridges 12 on circular segments 14 and 16 are provided to allow the locking ring 10 to be securely grasped between the thumb and finger of the user. Two substantially flat segments 13 and 15 are on opposing sides of the locking ring 10, between circular segments 14 and 16. Four flanges or guides 20a, 20b, 21a and 21b, extend inwardly from the flat segments 13 and 15 of the locking ring 10. Two of the flanges protrude inwardly from each flat segment 13 and 15 of the locking ring 10.

Located on each flange 20a, 20b, 21a and 21b is an inward protrusion 18. Both the protrusions 18 and flanges 20a, 20b, 21a and 21b are made of the same material as, and molded with, locking ring 10 in the preferred embodiment.

FIG. 3A is a perspective view of the locking ring 10 about to be mounted onto stem 28, wherein the plunger stem 28 does not have a plunger head 41 or plunger tip 42. Locking ring 10 will not slide onto stem 28 absent a pinching force on circular end segments 14 and 16, because protrusions 18 protrude to a narrower diameter than stem 28. To mount locking ring 10 onto stem 28, a pinching force is exerted on circular segments 14 and 16. Inward pinching forces on the circular segments 14 and 16 of locking ring 10 will cause inward movement of circular ends 14 and 16 as indicated by arrows 19 and 21. This, in turn, causes convex radial movement Of the flat segments 13 and 15. This pinching force causes radial outward displacement of protrusions 18, thereby increasing the separation of locking ring 10 between flat segments 13 and 16 and permitting locking ring 10 to slide along stem 28. FIG. 3B is a bottom view of the locking ring 10 mounted on the stem of FIG. 3A, in the preferred embodiment of the present invention.

Referring back to FIG. 2, cut-outs 22a and 22b are made in the center of each flat segment 13 and 15 in the preferred embodiment. Cut-outs 22a and 22b facilitate the radial expansion of flat segments 13 and 15 in reaction to forces applied as indicated by arrows 19 and 21.

Returning to FIG. 3A, locking ring 10 slides onto stem 28 with the flat segments 13 and 15 of locking ring 10 positioned over the vertical columns of grooves 37a and 37b. The flanges 20a, 20b, 21a and 21b protrude to engage the vertical lips 41. The outer edges of flanges 20a, 20b, 21a and 21b engage and track vertical lips 41 when the locking ring 10 is mounted on stem 28. Thus, locking ring 10 should not rotate axially about stem 28, and the protusions 18 on the flat sections 13 and 15 of the locking ring 10 remain positioned over the vertical columns of grooves 37a and 37b.

When no force is applied to the locking ring 10, the separation of the locking ring 10 between the protrusions 18 across flat segments 13 and 15 is less than the separations the inter-groove sections 39 of stem 28 (FIG. 3A). Thus, a pinching force must be exerted on the locking ring 10, causing convex radial movement across flat sections 13 and 15, for the locking ring 10 to be slidable over any inter-groove section 39 on stem 28.

When the locking ring 10 is positioned over a groove 36 and no pinching force is exerted on the locking ring, the flat segments 13 and 15 are positioned radially inward and the plurality of discrete protrusions 18 individually engage one of the grooves 36. Thus, when the locking ring 10 is at rest, the protrusions 18 can engage a groove 36. The locking ring 10 will not slide along stem 28 over inter-groove sections 39 when the protrusions 18 are mated with a groove 36 unless a pinching force is exerted upon circular segments 14 and 16. Therefore the locking ring 10 is fixed in place when the protrusions 18 engage a groove 36.

The user can position locking ring 10 in any of the grooves 36 by exerting the pinching force on circular segments 14 and 16 (indicated by arrows 19 and 21), sliding the locking ring 10 to the chosen groove 36, and releasing the locking ring 10. The protrusions 18 on locking ring 10 engage grooves 36 with an audible snap, informing the user that locking ring 10 is in place. In contrast, if the protrusions 28 are positioned over an inter-groove section 39 of stem 28, no "snap" occurs. The user will then slide the locking ring 10 along stem 28 until the notches 18 snap into the desired groove 36. Thus, the user knows when the locking ring 10 has engaged a groove 36 and is in position.

The grooves 36 are vertically spaced along stem 28 a selectable predetermined distance apart to provide for variable amounts of fluid to be injected from or drawn into syringe 8. The selected placement of each groove 36 corresponds to an exact predetermined amount of fluid in the syringe 8. As is known to those skilled in the art, numbers correlating to the amount of fluid that will be injected from or drawn into the syringe 8 may be placed on syringe barrel 50, as well as near the grooves 36 on stem 28.

FIG. 4 shows the top 49 of the syringe barrel 50 abutting locking ring 10. The locking ring 10 ensures that the proper amount of fluid is injected into the patient by precluding undesired downward motion of plunger 34, within the syringe barrel 50.

Even if one or more of the plurality of discrete protrusions 18 on the locking ring 10 are not properly mated to one of the grooves 36, but are accidentally positioned over an inter-groove section 39, a recovery mechanism is provided in the preferred embodiment of the present invention. If the syringe barrel 50 is forced into the locking ring 10 when the locking ring 10 is positioned over an inter-groove section 39, the locking ring 10 will slide across the inter-groove section 39 and the protrusions 18 engage the next groove 36 encountered.

Thus, if the user accidentally does not lock the locking ring 10 into a groove, the locking ring 10 still functions. The natural inward force present in the locking ring 10 causes this automatic engagement of the protrusions 18 with a groove 36. An automatically locking locking ring 10 is a safety feature thereby provided by the present invention.

In the preferred embodiment, this safety feature permits, at most, 1 cc too much fluid to be injected. In the preferred embodiment, the position of each groove 36 corresponds to 1 cc of fluid in the syringe barrel 50. If the locking ring 10 is accidentally placed over an inter-groove section 39 above the desired groove, and is thus not locked into position, a patient would be injected with, at most, 1 cc too much fluid, because the locking ring 10 should lock into the next available groove 36.

Another advantage of the present invention is that the locking ring 10 can be moved along stem 28 with no twisting motion and using only two fingers. This feature is especially important in angiographic surgery because it is often the case that a user will need to exert maximum upward or downward pressure on the plunger 34 while firmly holding the syringe barrel 50. It is awkward for the user to simultaneously use both hands to apply pressure on the control syringe and to perform complex rotational movements with their hands to control a locking mechanism.

For example, a user is often required to draw and hold a high-pressure vacuum using an angiographic control syringe. To form such a high-pressure vacuum, the user will place two fingers of one hand into the grasping rings 52a and 52b on the syringe barrel 50, and grab thumb ring 26 with the second hand. The user withdraws plunger tip 42 upward in the syringe barrel 50 to form the vacuum, and moves locking ring 10 downward to abut the syringe barrel 50, thereby precluding the plunger 34 from moving downward which would let the vacuum escape.

The locking ring 10 of the present invention can be slidably moved into the desired position using only two fingers. Therefore, the user can grasp the thumb ring 26 and still move the locking ring 10 with a finger and thumb from the same hand. Further, the absence of complex rotational movement to engage the locking ring 10 means the user does not have to adjust their grip on thumb ring 26 to lock the locking ring 10 into place. The user avoids having to try to grip and hold the syringe while simultaneously trying to make a rotational movement to lock a locking ring.

Figure 5:
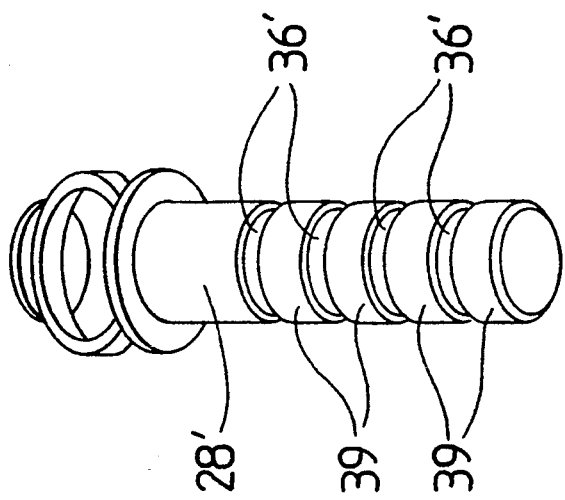
FIG. 5 is a perspective view of an alternative embodiment of the stem of the present invention.

FIG. 5 is a perspective view of an alternative embodiment of the stem 28' of the present invention. Annular grooves 36' circumscribe stem 28'. Locking ring 10 slides onto stem 28' and performs as described above, except that flanges 20a, 20b, 21a and 21b do not engage and track any portion of the stem 28'. The locking ring 10 can be affixed on stem 28' in any orientation, and the locking ring 10 may be fully rotated axially.

The embodiment if FIG. 5 creates a tactile sensation in the user's hand when the plunger 42 is vertically displaced within the syringe barrel 50. This tactile sensation is caused by the inter-groove segments 39' striking the syringe barrel 50. This distracting tactile sensation is not present in the preferred embodiment of the present invention because flat annular sections 38a and 38b slide smoothly against syringe barrel 50 during vertical displacement of the plunger (FIG. 1 ).

Referring to FIG. 6, the preferred embodiment of control syringe 8 also includes an improved plunger tip 42 and syringe barrel seat 56 designed to capture air bubbles in the injectate. Refer back to FIG. 1, which is a perspective view of the improved angiographic syringe 8 showing the plunger tip 42 and syringe barrel seat 56. FIG. 6 is a side view of FIG. 1 with the plunger tip 42 engaging seat 56 and wherein no luer connector is attached to syringe barrel 50.

The plunger tip 42 protrudes downward from side walls 43. When the plunger tip 42 is forced downward to engage seat 56, the plunger tip 42 engages syringe barrel opening 48, expelling injectate from the syringe 8 (FIG. 6).

In the preferred embodiment, the plunger tip 42 is highly frustoconical in shape. The seat 56 is slightly frustoconical in shape. The angle of the cone formed by plunger tip 42 is relatively more acute than the angle of the seat 56 of the syringe barrel 51. Because plunger tip 42 is highly frustoconical in shape, a circular air bubble retention cell 70 is formed between plunger tip 42 front walls 45 and seat 56 when the plunger tip 42 and seat 56 are fully engaged. Air in the syringe barrel 50 should be captured in cell 70, thereby reducing the likelihood of injecting air into the patient.

Those skilled in the art will recognize that the size of cell 70 may be altered by varying the frustoconical shape of either or both plunger tip 42 and seat 56. The seat 56 and plunger tip 42 must retain a slight frustoconical shape so air bubbles will rise away from opening 48 toward syringe barrel side walls 58.

While this invention is described in detail with particular reference to the preferred embodiment thereof, it will be understood that other variations and modifications can be made without departing from the spirit and scope of the invention as defined in the appended claims.

What is claimed is:

1. In an angiographic syringe, including a syringe barrel and a plunger slidably engaged with said syringe barrel, the plunger including a stem and a head, a locking mechanism, comprising:
    a substantially oblong locking ring positioned circumferentially on the stem of said plunger;
    a plurality of grooves formed on opposing sides of the stem of said plunger; and
    a pair of inward protrusions from said locking ring on opposing sides of said stem, said protrusions being movable outward concomitantly responsive to longitudinal compression of said locking ring, thereby permitting detachable engagement of said protrusions and of said grooves on opposing sides of said stem.

2. An angiographic syringe as recited in claim 1 wherein said locking ring is oblong in shape, having opposing substantially circular segments and opposing substantially flat segments, wherein said protrusions are positioned on said flat segments, and wherein said protrusions reciprocate radially in response to pressure on said substantially circular segments.

3. In an angiographic syringe including a syringe barrel and a plunger slidably engaged with said syringe barrel, the plunger including a stem and a head, a locking mechanism, comprising:
    a locking ring positioned on the stem of said plunger wherein said locking ring is oblong in shape, having opposing substantially circular segments and opposing substantially flat segment;
    a plurality of grooves on the stem of said plunger; and
    two protrusions extending inwardly from each of said substantially flat segments of said locking ring, said protrusions being movable outward, thereby permitting detachable engagement of said protrusions and any of said grooves on said stem wherein a cut-out is located on each of said substantially flat segments between said two protrusions, said cut-outs facilitating outward movement of said substantially flat segments in response to inward pressure on said substantially circular segments.

4. An angiographic syringe as recited in claim 1 wherein said grooves are positioned in two columns on opposing sides of said stem, with two annular, flat columns on opposing sides of said stem positioned between the columns of grooves, and wherein a lip is formed at the intersection of each said column of grooves and said annular flat column.

5. An angiographic syringe as recited in claim 4 wherein at least one guide flange protrudes inwardly from said locking ring to engage and track one of said lips.

6. An angiographic syringe as recited in claim 5 wherein a guide flange extends from adjacent each said protrusion, each flange engaging and tracking one of said lips when said locking ring is mounted on said stem.

7. In an angiographic syringe including a sizable barrel and a plunger slidably engaged with said syringe barrel, the plunger including a stem and head, a locking mechanism comprising;
    a plurality of grooves on the stem of said plunger;
    an oblong locking ring positionable on the stem of said plunger, said locking having opposing circular segments and opposing substantially flat segments with two opposed inward protrusions formed on each substantially flat segments, said locking ring being radially movable where said protrusions are positioned and wherein a cut-out is located on each of said substantially flat segments between said two protrusions, said cut-outs facilitating outward movement of said substantially flat segments in response to inward pressure on said substantially circular segments.

8. In an angiographic syringe, including a syringe barrel and a plunger slidably engaged with said syringe barrel, the plunger including a stem and a head, a locking mechanism comprising;
    a plurality of grooves on the stem;
    an oblong locking ring positionable on the stem of said plunger;
    a pair of opposing inward protrusions formed on said locking ring; and
    means for facilitating concomitant radial movement of said protrusions responsive to variation in the elongation of said locking ring to detachably engage opposing grooves on said stem.

* * * * *